United States Patent
Thompson

[11] Patent Number: 5,471,997
[45] Date of Patent: Dec. 5, 1995

[54] METHOD OF CONTRACEPTION

[76] Inventor: Leif H. Thompson, P.O. Box 148, Philo, Ill. 61864

[21] Appl. No.: 426,283

[22] Filed: Apr. 21, 1995

[51] Int. Cl.⁶ .................................................. A61F 6/02
[52] U.S. Cl. ............................................. 128/842; 128/843
[58] Field of Search ................................... 128/842, 843, 128/844, 918, 830–841; 604/347–353

[56] References Cited

U.S. PATENT DOCUMENTS

| | | | |
|---|---|---|---|
| 3,589,355 | 6/1971 | Lee | 128/843 |
| 3,687,129 | 8/1972 | Nuwayser | 128/843 |
| 3,815,578 | 6/1974 | Bucalo | 128/843 |
| 3,990,434 | 11/1976 | Free | 128/843 |
| 4,013,063 | 3/1977 | Bucalo | 128/843 |
| 4,200,088 | 4/1980 | Denniston | 128/843 |
| 4,512,342 | 4/1985 | Zaneveld | 128/843 |
| 4,682,592 | 7/1987 | Thorsgard | 128/843 |

*Primary Examiner*—Michael A. Brown
*Attorney, Agent, or Firm*—Philip L. Bateman

[57] ABSTRACT

Conception is prevented in male mammals by making an incision in one wall of the vas deferens near the epididymis and inserting a filament into the vas deferens through the incision. The filament has a length at least about one-fourth the length of the vas deferens and an outside diameter about equal to the inside diameter of the vas deferens. It contains an enlargement at one end and is made of a material inert to tissue. The filament is inserted into the vas deferens all the way to the enlargement. The incision remains open around the filament to permit sperm to escape from the vas deferens.

7 Claims, 1 Drawing Sheet

METHOD OF CONTRACEPTION

FIELD OF THE INVENTION

This invention relates to contraception. More particularly, this invention relates to a method of contraception involving the placement of a filament in the vas deferens of a male mammal.

BACKGROUND OF THE INVENTION

Mammals reproduce by sexual intercourse. During sexual intercourse, the male inserts his penis into the female's vagina and ejaculates millions of sperm. Conception occurs if one of the sperm fertilizes an ovum (the female egg). After fertilization, the embryo becomes implanted in the female's uterus and begins to develop. Sperm are produced in the testes and travel through a number of ducts before leaving the body. Upon leaving a testis, sperm first travel through the epididymis, a coiled duct lying on the lateral edge of the testis. Sperm then travel through the vas deferens, a tube having a relatively small lumen (internal passageway) and a thick muscular coat which runs upward to a location just above the prostate gland. The vas deferens contains an enlarged section, known as the ampulla, near the point where the seminal vesicle joins. The common duct formed by the union of the vas deferens and seminal vesicle is known as the ejaculatory duct. The two ejaculatory ducts open into the urethra. The urethra runs the length of the penis and opens at its tip. Sperm continually enter the epididymis and, to a lesser degree, the vas deferens. During ejaculation, peristaltic muscular contractions force the sperm to flow through the vas deferens and the urethra.

It is sometimes desirable to prevent conception during sexual intercourse. In the case of certain livestock, man often wants to control which male animal fertilizes a female. In the case of man himself, one or both partners may want to prevent conception and pregnancy. There are many methods of contraception currently practiced. One of the most effective methods is to prevent the flow of sperm through the vas deferens. In a surgical procedure known as a vasectomy, the vas deferens is cut, a section is removed, and the two loose ends are sealed shut. This procedure is relatively safe and is performed relatively easily. Unfortunately, a vasectomy suffers from one very serious disadvantage—it usually cannot be successfully reversed.

There are several factors contributing to the irreversibility of a vasectomy. First, it is difficult to reconnect the two severed ends of the vas deferens. Second, the "downstream" segment of the vas deferens (the segment joining the ejaculatory duct and urethra) tends to necrose over time. This necrosis occurs because the blood supply and nerves supplying the vas deferens are disrupted by the severance. A necrotic section of vas deferens is unable to convey sperm and is very difficult to repair. Third, the "upstream" segment of the vas deferens (the segment communicating with the epididymis) also tends to necrose over time. This necrosis occurs because the testis continues to produce sperm and the sperm continue to flow into the vas deferens. Without an exit, pressure builds within and enlarges and weakens the vas deferens. The vas deferens eventually ruptures, in a manner analogous to an over-inflated balloon. A ruptured vas deferens is nearly impossible to repair.

A number of devices have been disclosed which attempt to control the flow of sperm through the vas deferens, and yet provide a reversibility lacking in a vasectomy. One type of such devices are plugs (also known as intra-vasal occlusion devices) which are inserted into the vas deferens through an incision. These plugs offer the advantage of not requiring a complete severance of the vas deferens. Unfortunately, the plugs suffer from one of two disadvantages: They either permit sperm to pass or they lead to a necrosis and rupturing of the vas deferens.

Braley, U.S. Pat. No. 3,422,813, issued Jan. 21, 1969; Brodie, U.S. Pat. No. 3,648,683, issued Mar. 14, 1972; and Bucalo, U.S. Pat. No. 3,877,461, issued Apr. 15, 1975; disclose intra-vasal plugs. However, the upstream pressure in the vas deferens eventually expands the vas deferens in the vicinity of the plug, allowing sperm to bypass the plug. As a result, these plugs do not completely stop the emission of sperm during ejaculation.

Other plugs are specifically designed to stop the bypassing of sperm caused by expansion of the vas deferens. As one example, Nuwayser, U.S. Pat. No. 3,687,129, issued Aug. 29, 1972, discloses a plug having a fabric coating which allows for the in growth of cells from the wall of the vas deferens. Other examples include Lee, U.S. Pat. No. 3,589,355, issued Jun. 29, 1971; Denniston, Jr., U.S. Pat. No. 4,200,088, issued Apr. 29, 1980; and Zaneveld, U.S. Pat. No. 4,512,342, issued Apr. 23, 1985. These three patents disclose plugs containing various features preventing the vas deferens from expanding around the plug. These plugs may succeed in forming a total barrier. However, pressure increases upstream of the plug and the vas deferens enlarges and eventually ruptures.

Valves and filters are other types of intra-vasal devices which attempt to control the flow of sperm through the vas deferens and yet provide reversibility. Bucalo, U.S. Pat. No. 4,024,855, issued May 24, 1977, discloses a valve which completely shuts off the flow of fluid when closed. Bucalo, U.S. Pat. No. 3,991,743, issued Nov. 16, 1976; and Bucalo, U.S. Pat. No. 4,013,063, issued Mar. 22, 1977; disclose filters which are mounted in the vas deferens and which retain sperm, but let other parts of the fluid pass. None of these valves or filters has achieved any widespread usage. It is believed that all these devices plug relatively quickly and eventually lead to a rupturing of the upstream portion of the vas deferens.

Accordingly, a demand still exists for a method of contraception for males which is as effective as a vasectomy, but is easily and successfully reversed.

SUMMARY OF THE INVENTION

The general object of this invention is to provide an improved method of contraception. A more particular object is to provide an improved method for reversibly preventing the ejaculation of sperm from male mammals. Other objects are to provide a method which does not require the vas deferens to be cut in two and which does not result in a necrosis or rupturing of the vas deferens.

I have invented a method of contraception for mammals having a vas deferens for carrying sperm from a testis to a urethra. The method comprises: (a) providing a filament having a length at least about one-fourth the length of the vas deferens, the filament having an outside diameter about equal to the inside diameter of the vas deferens, the filament being of a material inert to tissue, and the filament having an enlargement at one end; (b) making an incision in one wall of the vas deferens near the epididymis, the incision having a length greater than the outside diameter of the filament and less than the width of the enlargement so that the filament, but not the enlargement, can fit through the incision; and (c)

inserting the filament into the vas deferens through the incision so that the filament extends from the incision toward the urethra, so that the enlargement remains outside and adjoining the vas deferens, and so that the incision remains open around the filament to permit sperm to escape from the vas deferens.

This method effectively prevents the emission of sperm from male mammals during ejaculation and yet is highly reversible. Three factors contribute to the high reversibility. First, the vas deferens is not cut in two so there is no need for a reconnection. Second, the vas deferens does not necrose because the blood supply and nerves remain intact. And third, the vas deferens near the epididymis does not enlarge, necrose, and rupture because sperm are permitted to escape through the incision.

DETAILED DESCRIPTION OF THE INVENTION

Figure 1:
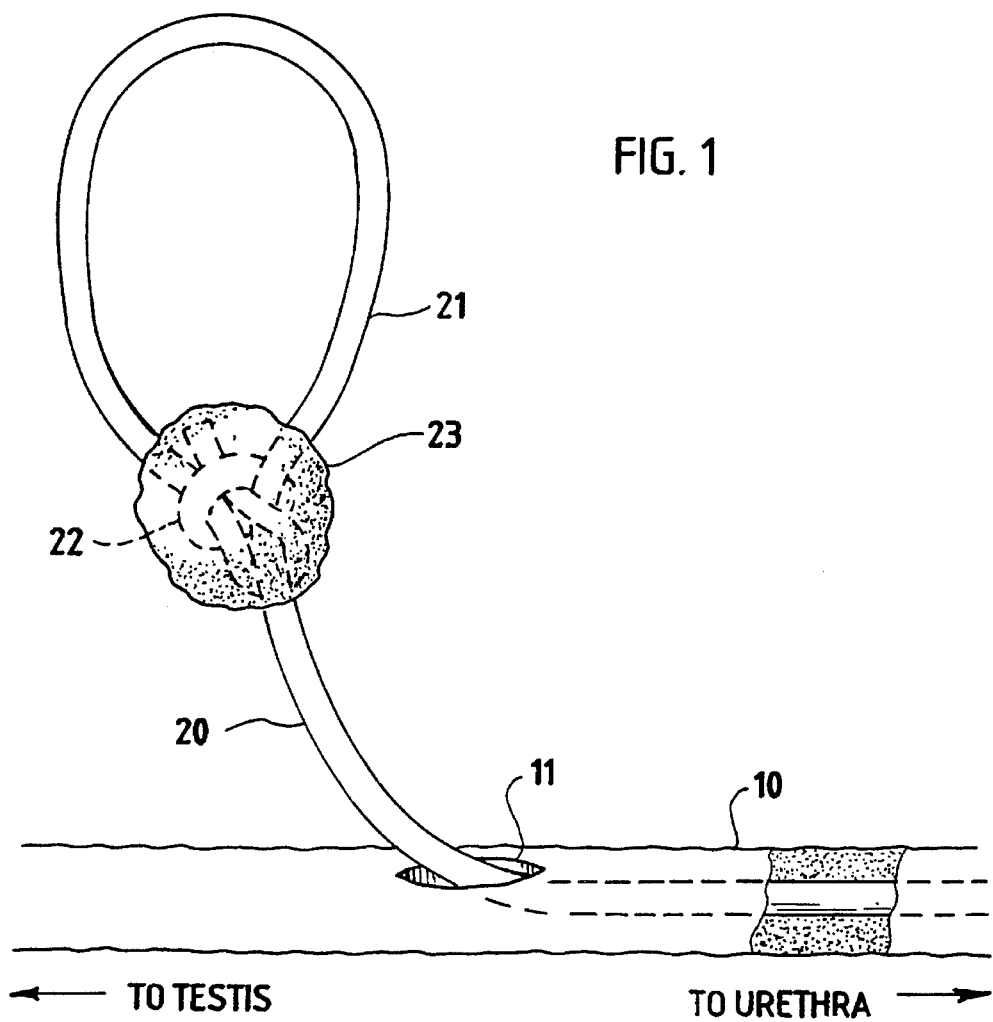
FIG. 1 is a perspective view of an elongated filament being inserted into the vas deferens in accordance with the method of this invention.
Figure 2:
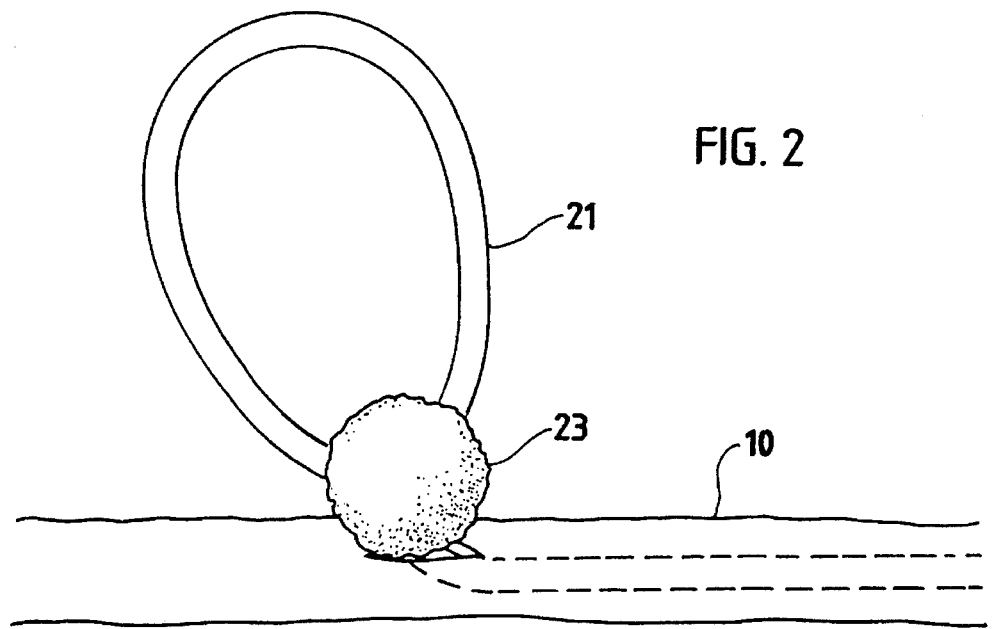
FIG. 2 is a perspective view showing the elongated filament fully inserted into the vas deferens.

This invention is best understood by an initial reference to the drawings. In FIG. 1, a section of the vas deferens 10 near the epididymis of a human male is shown. An incision 11 has been made in one wall of the vas deferens. One end of a section of filament 20 is inserted through the incision and into the lumen of the vas deferens and then fed in the direction of the urethra. The other end of the filament has been formed into a loop 21 and tied into a knot 22. The knot is secured with a dab of rubber glue 23 which completely surrounds the knot. In FIG. 1, the filament is shown in the process of being inserted into the vas deferens. In FIG. 2, the filament is shown fully inserted. It can be seen that the loop and the rubber-encased knot remain on the outside of the vas deferens at all times and that the incision remains open. The open incision around the filament provides a vent for sperm to escape, thereby preventing an enlargement and rupturing of the vas deferens. The portion of the filament inside the vas deferens blocks the flow of sperm. The muscular contractions of the vas deferens and other tissue impart movement in the direction from the testis to the urethra so that the filament tends to be pulled tightly against the incision rather than being expelled. Accordingly, the filament remains in place indefinitely until surgically removed.

The invention can now be considered in more detail. Access to the vas deferens is gained by making an incision in the scrotum and exposing a short (approximately one cm) section of the vas deferens. It is desirable to expose a section of the vas deferens as close to each epididymis as possible so that an incision can be made in the vas deferens near the epididymis. The term "near" means the incision is closer to the epididymis than to the urethra, i.e., in the first one-half of the length of the vas deferens. The incision is preferably made in the first one-fourth of the vas deferens. It is most preferred to minimize the distance between the filament insertion point and the epididymis, thereby maximizing the distance to the end of the vas deferens.

The incision in the vas deferens extends completely through one wall to reach the lumen. The size of the incision is large enough to enable the filament to be inserted. The size of the incision is small enough to prevent the looped (or otherwise enlarged) end of the filament from fitting through it. In most cases, the length of the incision is about 1½ to 4 times the diameter of the filament. The length of the incision is preferably about 2 to 3 times the diameter of the filament. The width of the incision is preferably minimized by making a single slit using a sharp instrument.

The portion of the filament inserted into the vas deferens has a length at least about one-fourth the length of the vas deferens so a sufficiently-effective blockage is made. If the filament length is too short, significant amounts of sperm may pass over the filament and conception may occur. The filament does not extend past the end of the vas deferens— any blockage of the ejaculatory duct is to be avoided. The portion of the filament inserted into the vas deferens preferably has a length of about 0.5 to 0.9 times the length of the vas deferens. The portion inserted most preferably has a length of about 0.7 to 0.8 times the length of the vas deferens. The length of the vas deferens varies from species to species, and from individual to individual. For example, in man, the length of the vas deferens is about 8 to 10 cm and, in sheep, the length is about 16 to 20 cm. Accordingly, the preferred filament length for man is about 4 to 9 cm, and for sheep, about 8 to 18 cm.

The filament is preferably round in cross-section because this shape best conforms to the lumen. The outside diameter of the filament is about equal to, or slightly less than, the inside diameter of the lumen. As with length, the inside diameter of the vas deferens varies from species to species, and from individual to individual. In man, the lumen diameter is typically about 0.5 to 2.5 mm. Accordingly, the preferred filament diameter for man is about 0.25 to 2.5 mm. Smaller filament diameters tend to be slightly easier to insert while larger diameters tend to provide better blockage.

The filament is made of a material which is inert to the vas deferens and surrounding tissue. In other words, the material causes no adverse reaction from these tissues and there is no growth of tissue to or on the material. The material is stiff enough to enable the filament to be fed into the vas deferens and yet flexible enough to conform to the curved shape of the vas deferens. Suitable materials include plastics, such as nylon and Teflon; metals, such as copper and copper alloys; natural materials; combinations thereof, such as plastic-coated metals; and the like. Plastics are preferred because of their low cost, stiffness, and flexibility. Nylon is the most preferred material because of its ready availability in a wide range of diameters.

At least a portion of the filament inserted into the vas deferens is solid in cross-section so that sperm cannot travel through the filament. The filament may be solid throughout or a portion of the filament may be hollow or porous. If desired, the filament contains a material having spermicidal and/or anti-viral properties. Examples of suitable spermicides include those listed in columns 58 of Bucalo, U.S. Pat. No. 3,877,461, issued Apr. 15, 1975. Such materials are conveniently added to the filament if a portion of the filament is hollow or porous.

One end of the filament contains an enlargement whose purpose is to keep a portion of the filament outside the vas deferens at all times. The enlargement is large enough that it does not pass through the incision. Suitable enlargements are created in many different ways. One way is to simply tie a knot in the end of the filament. A second way of creating an enlargement is to compress and/or melt the end of the filament to form a mass or head. A third way is to attach an object or mass to the filament. As shown in FIG. 1, a preferred enlargement is created by a combination of these methods. First, a bowline knot is formed. This type of knot includes a loop. Next, a drop of gelling compound such as Silastic silicone rubber glue, a product of the Dow Corning Corporation, is added to the knot and allowed to harden. The hardened rubber both secures the knot and increases the size of the enlargement. The loop ensures the end of the filament remains outside the vas deferens and also eases removal of the filament because it is so easy to grasp.

As previously mentioned, the filament passing through the wall of the vas deferens ensures that the incision in the wall remains open. In this sense, the filament acts in a manner analogous to an earring. When the external object (the filament or earring) is in place, the tissue (the vas deferens or ear lobe) remains open. But when the external object is removed, the tissue eventually closes. The opening in the vas deferens contributes to the reversibility of this method of contraception. Sperm are continuously being forced into the upstream end of the vas deferens. Without a vent, pressure builds and the vas deferens enlarges and eventually ruptures. But with a vent, sperm flow out of the vas deferens into the scrotum and are absorbed by the surrounding tissue.

With the filament in place in accordance with this invention, the number of sperm emitted during ejaculation is insufficient to present any appreciable chance of conception. There is virtually no damage to the vas deferens over time with the filament in place. The upstream portion of the vas deferens does not rupture because the sperm are vented outside the vas deferens. The downstream portion of the vas deferens remains healthy because the small incision causes minimal disruption of nerves and blood supply.

If and when the fecundity of the male is to be restored, the reversal procedure is even simpler than the original procedure. An incision is made in the scrotum, the enlarged end of the filament is grasped, and the entire filament is removed. The incision will shut over time or, if an immediate closure is desired, the incision may be sutured. In either case, fecundity is restored immediately because the entire vas deferens remains intact and functional while the filament is in place.

EXAMPLE

This example illustrates the contraceptive effectiveness of the method of this invention on sheep. The experiment contained four parts. First, three male sheep ("rams") were given a unilateral vasectomy (a vasectomy of only one vas deferens). Second, the continued fertility of the males due to their remaining functional vas deferens was established. Third, the rams were subjected to the contraceptive method of this invention. Finally, it was confirmed that the males would not impregnate female sheep ("ewes").

Three rams having an age of approximately seven months were selected. They were given a light dose of xylazine analgesic by intra-muscular injection to induce a general anesthetic state. They were then restrained on their backs in a cradle and their scrotal and groin areas were scrubbed and disinfected. A small incision of less than one cm was made on the anterior ventral face of the scrotum on the left side about one cm off the midline to the depth of the testicular face. The vas deferens was identified and excised with a curved hemostat and approximately two cm removed. Each male received five cc of penicillin and was provided feed and water as normal for two weeks of recovery.

After recovery from the unilateral vasectomy, each ram was mated to five fertile ewes. Estrous activity in the large pool of ewes was checked twice daily with a "teaser" male. Once a ewe was identified as being receptive for mating, she was placed with the designated ram and two to four successful matings were allowed. Each ram mated no more than two females per day. The mating to establish fertility was accomplished within one week.

After the mating, the females were observed with a teaser male to determine if they returned to estrus around day 16 after mating. All five females that were mated to each of two males failed to return to estrus (indicating a 100% conception rate), while only two of the five mated to the third male failed to return to estrus (indicating a 40% conception rate). Later, one of the three ewes which returned to estrus continued to recycle when mated to other fertile rams not a part of this experiment, indicating the problem was with the ewe. Accordingly, the conception rate with the third male should be considered 50% (2 of 4) rather than 40% (2 of 5).

Seven weeks after the initial mating, the three rams were again prepared for surgery as previously described. A nylon filament having a length of about 15 cm and an outside diameter of 0.5 mm was obtained. A bowline knot was tied in one end with a loop of about i cm. A drop of Silastic silicone rubber was added to completely enclose the knot and allowed to harden. An incision of about 1 mm was made lengthwise in the vas deferens at a point close to the epididymal end of the vas deferens. The filament was then placed in the lumen of the vas deferens. The end of the filament containing the knot remained outside the incision. By so positioning the filament, the incision remained open to allow sperm to escape from the vas deferens as the pathway of least resistance.

The three rams were then allowed to mate a new group of ewes during the three week period after insertion of the filament. As before, receptive ewes were detected as being in estrus by the use of a teaser male. Each ram was mated to seven ewes (no more than one ewe per day with a two-day interval between ewes). Each ewe was mated to the ram at least twice when first detected in estrus and most were mated twice again 12 hours later.

When checking these ewes 16 days later, 20 of the 21 returned to estrus on schedule.

During the matings, the rams were observed to display no signs of discomfort or hesitation during copulation. Libido was normal and no urogenital problems associated with the filament appeared.

CLAIMS

I claim:

1. A method of contraception for mammals having a vas deferens for carrying sperm from a testis to a urethra, the method comprising:

(a) providing a filament having a length at least about one-fourth the length of the vas deferens, the filament having an outside diameter about equal to the inside diameter of the vas deferens, the filament being of a material inert to tissue, and the filament having an enlargement at one end;

(b) making an incision in one wall of the vas deferens near the epididymis, the incision having a length greater than the outside diameter of the filament and less than the width of the enlargement so that the filament, but not the enlargement, can fit through the incision; and (c) inserting the filament into the vas deferens through the incision so that the filament extends from the incision toward the urethra, so that the enlargement remains outside and adjoining the vas deferens, and so that the incision remains open around the filament to permit sperm to escape from the vas deferens.

2. The method of claim 1 wherein the filament has a length of about 0.5 to 0.9 times the length of the vas deferens.

3. The method of claim 2 wherein the enlargement comprises a knot.

4. The method of claim 3 wherein the filament material is nylon.

5. The method of claim 4 wherein the filament has a diameter of about 0.25 to 2.5 mm.

6. The method of claim 1 wherein the mammal is a human being and the filament has a length of about 4 to 9 cm and a diameter of about 0.25 to 2.5 mm.

7. The method of claim 6 wherein the filament contains spermicidal or anti-viral agents.

* * * * *